US008227065B2

(12) United States Patent
Keener et al.

(10) Patent No.: US 8,227,065 B2
(45) Date of Patent: *Jul. 24, 2012

(54) ADHESIVE TAPE

(75) Inventors: Phillip R. Keener, Chapin, SC (US); William C. Gadson, Union, SC (US); Charles B. Jenkinson, Jr., Evans, GA (US); Robert G. McCrary, LaGrange, GA (US); Jerry Mickle, Newnan, GA (US)

(73) Assignee: Milliken & Company, Spartanburg, SC (US)

( * ) Notice: Subject to any disclaimer, the term of this patent is extended or adjusted under 35 U.S.C. 154(b) by 53 days.

This patent is subject to a terminal disclaimer.

(21) Appl. No.: 12/852,592

(22) Filed: Aug. 9, 2010

(65) Prior Publication Data

US 2011/0195625 A1 Aug. 11, 2011

Related U.S. Application Data

(63) Continuation-in-part of application No. 12/658,313, filed on Feb. 8, 2010.

(51) Int. Cl.
- *B32B 9/00* (2006.01)
- *B32B 7/12* (2006.01)
- *B32B 33/00* (2006.01)

(52) U.S. Cl. .......... 428/40.1; 428/343; 428/354

(58) Field of Classification Search .......... 428/40.1, 428/41.8, 43, 343, 352, 354
See application file for complete search history.

(56) References Cited

U.S. PATENT DOCUMENTS

| | | | | |
|---|---|---|---|---|
| 4,303,712 | A | 12/1981 | Woodroof | 428/58 |
| 4,439,482 | A * | 3/1984 | Suematsu | 442/60 |
| 4,654,254 | A | 3/1987 | Gerry et al. | 428/252 |
| 4,967,740 | A | 11/1990 | Riedel | 128/156 |
| 5,354,597 | A | 10/1994 | Capik et al. | 428/152 |
| 5,611,356 | A | 3/1997 | Rothrum | 128/849 |
| 5,648,167 | A | 7/1997 | Peck | 428/355 |
| 5,795,834 | A | 8/1998 | Deeb et al. | 442/62 |
| 5,910,125 | A | 6/1999 | Cummings et al. | 602/58 |
| 5,947,917 | A | 9/1999 | Carte et al. | 602/52 |
| 5,985,775 | A | 11/1999 | Deeb et al. | 442/151 |
| 6,048,806 | A | 4/2000 | Deeb et al. | 442/151 |
| 6,063,492 | A | 5/2000 | Kurihara et al. | 428/343 |
| 6,171,985 | B1 | 1/2001 | Joseph et al. | 442/346 |
| 6,635,334 | B1 | 10/2003 | Jackson et al. | 428/136 |
| 6,672,952 | B1 | 1/2004 | Masmar et al. | 451/539 |
| 6,699,801 | B1 * | 3/2004 | Kawaguchi et al. | 442/2 |
| 7,056,526 | B2 | 6/2006 | Kuroda et al. | 424/443 |
| 7,056,844 | B2 | 6/2006 | Sheely | 442/58 |
| 7,078,582 | B2 | 7/2006 | Stebbings et al. | 602/57 |
| 7,181,933 | B2 | 2/2007 | Callaway et al. | 66/193 |
| 2002/0098349 | A1 | 7/2002 | Watanabe et al. | 428/343 |
| 2002/0164446 | A1 | 11/2002 | Zhou et al. | 428/40.1 |
| 2003/0026967 | A1 | 2/2003 | Joseph et al. | 428/292.1 |
| 2005/0227559 | A1 | 10/2005 | Ternon et al. | 442/149 |
| 2008/0131488 | A1 | 6/2008 | Kawamura et al. | 424/443 |

FOREIGN PATENT DOCUMENTS

| WO | WO 97/12561 | 4/1997 |
|---|---|---|
| WO | WO 98/46159 | 10/1998 |

* cited by examiner

*Primary Examiner* — Patricia Nordmeyer
(74) *Attorney, Agent, or Firm* — Cheryl J. Brickey

(57) ABSTRACT

A tape having a woven fabric and an adhesive on at least one side of the fabric. The woven fabric comprises polyester warp yarns and acetate weft yarns.

14 Claims, 1 Drawing Sheet

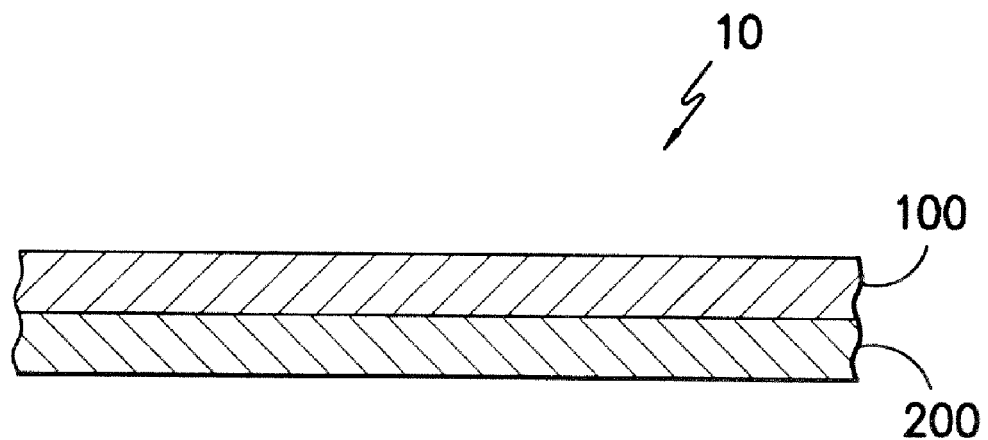
FIG. -1-
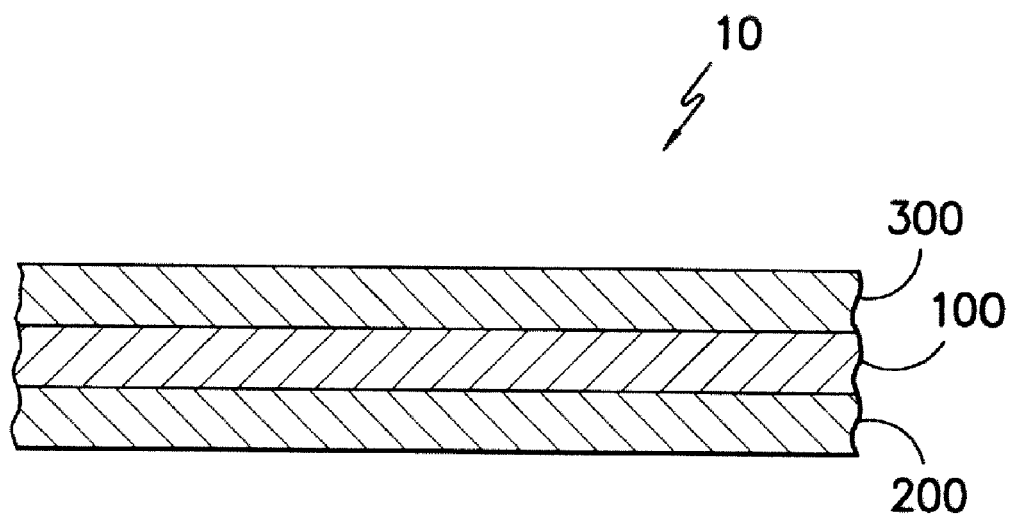
FIG. -2-

ADHESIVE TAPE

This application is a continuation in part of application Ser. No. 12/658,313, filed on Feb. 8, 2010.

FIELD OF THE INVENTION

The present invention generally relates to adhesive tapes. More particularly the invention relates to adhesive tapes that are well-suited for gaffer uses and are hand tearable in the cross-web and in the web direction.

BACKGROUND

Cloth or cloth-like tapes are useful in numerous applications. For example, cloth-like tapes are used in medical applications where they typically are adhered to skin. Most of the uses of cloth adhesive tapes in the medical market are for securing medical devices and light immobilization support. Some typical applications include securing endotracheal tubes, nasogastric tubes, and chest tubes, stabilizing body splints, and anchoring bulky wound dressings. Cloth or cloth-like tapes are also used in industrial and commercial applications such as in duct tapes, strapping tapes, electrical tapes, general utility tapes and in abrasives to name a few. Traditionally tapes, especially medical tapes, have been made out of an all acetate yarn construction. There is a need for a thin, inexpensive tape having high degrees of conformability.

Cloth or cloth-like tapes are useful in gaffer type applications. These applications require colored (including black) substrates with a non-glare finish. There is a need for a thin, inexpensive tape to meet these needs.

BRIEF SUMMARY

The present invention provides a tape having a woven fabric and an adhesive on at least one side of the fabric. The woven fabric comprises polyester warp yarns and acetate weft yarns.

BRIEF DESCRIPTION OF THE DRAWINGS

FIGS. 1 and 2 illustrate schematically cross-sections of exemplary adhesive tapes.

DETAILED DESCRIPTION

Referring now to FIG. 1, there is shown an embodiment of the tape 10 having a fabric 100 and an adhesive 200 on one side of the woven fabric 100. This tape 10 may be used in multiple adhesive tape applications, including but not limited to, medical tape, duct tape, gaffer tape, double sided tape, harness wrap, athletic tape, or any tape requiring a full face fabric. Preferably, the tape 10 is a medical tape. Medical tape is used extensively by medical professionals and consumers to attach devices or bandages to the skin, and protect the skin as may be required. This wide variety of usage requires that the tape have an adequate tensile and still tear easily by hand in the cross web and web direction for convenience and ease of application. It should be thin and conformable to allow for application and comfort to all parts of the body including fingers and toes. In another embodiment, the tape 10 is preferably a gaffer tape.

Using PET yarns in the warp enables the enhancement of the thinness and conformability of the tape while maintaining the adequate tape tensile and ease in hand tear ability. Typically, a PET yarn will have a higher tensile per denier allowing for the use of smaller yarns in the tape. It has been found that a 75 denier acetate yarn will deliver 0.19 lbs of tensile strength per end while a 40 denier PET yarn will deliver 0.35 lbs end. Using a smaller denier PET yarn and fewer ends to achieve the same tensile generates a number of positive attributes of the tape. Product conformability is enhanced versus all acetate constructions due to the high elongation of PET warp yarns. The PET warp yarns also allow for the fabric to be thinner than the all acetate tapes and can be used in sensitive and hard to reach areas. Typical thickness for acetate tape is 6 to 8 mils while PET/acetate tapes are 4 to 6 mils. The thinness comes from being able to use PET warp yarns (which are lower denier) which deliver adequate tensile strength while not requiring excessive amount of warp ends. It has also been found that using PET warp yarns versus acetate warp yarns allow for lower material costs and improved process ability in fabric formation; therefore, The PET/acetate tapes are generally less expensive than all acetate tapes. The polyester yarns may be textured.

The term "tape" as referred to above and below describes supported or unsupported, essentially two-dimensional articles such as sheets, strips, ribbons or die-cut parts (i.e., the extension of the articles in two directions distinctly exceeds the extension in the third direction).

The fabric 100 is selected to give the desired tear strength, tearing characteristics, tensile strength, and cover. The tape 10 is generally torn across the warp yarns, but at times is torn across the filling yarns. Smooth, easy tear is more closely related to the tear characteristics of the individual warp yarns and the close proximity of each warp yarn to each other. Ideal tear characteristic is similar to the smooth action of a zipper. Preferably, the tape is hand tearable in both directions (warp and fill). Preferably, the fabric 100 has a tensile strength of between about 5 lbs/inch and 80 lbs/inch preferably between 18 and 60 lbs/inch and a cover of between about 8 and 100 gm/m$^2$. Preferably the fabric 100 has a warp tear strength of 0.400 lb$_f$ to 1.400 lb$_f$.

The fabric 100 is a woven fabric. Preferably, the woven fabric is a plain weave. The plain weave has been shown to provide a flat smooth surface for application of the adhesive and improve the hand tear ability of the tape. Any other weave is also contemplated including but not limited to sateen weave, basket weave, and twill weave.

The woven fabric 100 contains polyester warp yarns. These polyester warp yarns are preferably continuous and may be monofilament or multifilament. Mono and multi filament warp yarns are clean and lint free which reduces contamination and potential defects in the tape. Their natural state is white which is a preferred feature in medical tapes. In one embodiment, the woven fabric contains polyester warp yarns in addition to other types of warp yarns, but in another embodiment the warp yarns are all polyester warp yarns. The warp yarns may have any cross-sectional shape including round, elliptical, square, tape shaped, tear-shaped, crescent-shaped, rectangular, regular or irregular, and multi-lobal. The polyester warp yarns 105 have a linear mass density of between about 20 and 100 denier, more preferably between about 20 and 90 denier. In another embodiment, the polyester warp yarns are less than about 70 denier, more preferably less than 45 denier. Having a low denier warp yarn has been shown to produce tapes 10 having good tear properties. The woven fabric 100 has a warp constructions having between about 50 and 130 ends per inch. In another embodiment, the woven fabric 100 has between about 60 and 90 ends per inch. In one embodiment, the warp yarns have an elongation at break of about 5% to 50%, more preferably about 15% to 30%.

It has been found that the monofilament warps may be woven in a wide range of fabrics without additional preparation requirements or sizing. In one embodiment, the warp yarns have no sizing or other protective ingredients and are not subjected to a slashing operation. Alternatively, the warp yarns are sized and processed with a slashing process.

The weft yarns in the woven fabric 100 contain acetate yarns. Acetate is cellulose tri-acetate, also referred to as tri-cellulose acetate. The weft yarns may be continuous or staple and may be monofilament, multi-filament, or spun. The characteristics of the weft yarns are selected based on the need of the final tape product. In one embodiment, the woven fabric contains acetate weft yarns in addition to other types of weft yarns, but preferably the weft yarns are all acetate weft yarns. The woven fabric 100 preferably has weft constructions having between about 5 and 100 picks per inch, more preferably between about 30 and 65 picks per inch. In one embodiment, the weft yarns are between about 40 and 300 denier. In another embodiment, the weft yarns are between about 100 and 200 denier. In one embodiment, the fabric is a 60×48 construction and in another embodiment, the fabric is in a 72×54 construction.

The woven fabric 100 is preferably a full face fabric having a small percentage of the surface area being "open" which means that there are very few areas in the fabric 100 having holes where there are no yarns in that area. Preferably, the fabric 100 has less than 15% open area, more preferably less than 10%, more preferably less than 5% open area. In the application of gaffer tape, having a low percentage of area being "open" is important so as to not show the adhesive through the tape.

In one embodiment, the fabric 100 is colored. In a gaffers tape this may be black, yellow, or any other suitable color. Preferably the fabric 100 color matches the polymer coating 300 color. The color in the fabric may be formed using colored yarns or the finished fabric may be colored. The yarns and/or fabric may be colored using any known technique including solution dyeing, pigment coating, jet dyeing, ranging dyeing, continuous dyeing, and disperse dyes for yarn penetration. Preferably, the color in the fabric is "through and through" meaning that the entire yarns, both the surface and throughout the diameter are colored.

The adhesive 200 as shown in FIG. 1 may be on one side of the fabric 100, or may be on both sides of the fabric 100. The adhesive may be applied to just the surface of the fabric 100, may penetrate a set percentage into the fabric 100, or migrate through the fabric onto the other side. Different adhesives may be used on either side. The adhesive 200 may be any suitable adhesive including but not limited to pressure-sensitive, heat cured and UV cured. Preferably, the adhesive 200 is a pressure-sensitive adhesive. Examples of pressure-sensitive adhesives that can be used in the present invention include rubber pressure-sensitive adhesives (natural rubber, polyisoprene rubber, styrene-butadiene rubber, SIS-, SBS- or SEBS-block rubber, butyl rubber, polyisobutylene rubber, reclaimed rubber), rubber gum adhesives, non-latex-based synthetic adhesives acrylic pressure-sensitive adhesives and silicone pressure-sensitive adhesives. The pressure-sensitive adhesive 200 is preferably tacky at room temperature and can be applied to a wide variety of substrates by exerting, for example, finger pressure. In one embodiment, the adhesive is white and in another embodiment the adhesive is clear. In another embodiment, the adhesive is colored and matches the fabric color and/or the coating color.

The pressure-sensitive adhesive 200 may be applied to the woven fabric 100 by any suitable method, such as but not limited to, solvent coating in a continuous or discontinuous method, roller coating, air knife coating, rod coating, electrostatic coating, slide hopper coating, extrusion coating, blade coating, curtain coating, and slide coating.

In one embodiment, the pressure-sensitive adhesive tape 10 has a release agent in contact with the pressure-sensitive adhesive 200. The release agent may be release liner, release chemical, or other material facilitating release of the pressure-sensitive adhesive off of a liner or application (such as skin). If the release agent is a liner, the release liner should be chosen such that the release liner may easily be stripped off the tape 10 without damaging the tape 10. Examples of suitable materials for use as a release liners include, e.g., paper (e.g., kraft paper), polymer films (e.g., polyethylene, polypropylene and polyester), composite liners, and combinations thereof that may optionally have a silicone or silicone containing material, a fluorinated or fluorine-containing material, or a fluorosilicone material on at least one of the surfaces. One example of a useful release liner is a fluoroalkyl silicone polycoated paper. In some constructions, the release liner includes a kraft paper sandwiched between two polymer films that have been treated to exhibit release properties. Release liners can optionally include a variety of markings and indicia including, e.g., lines, art work, brand indicia, and other information.

In one embodiment, the woven fabric 100 may have a thermoplastic layer on the side of the fabric 100 opposite the adhesive 200. This thermoplastic layer is preferably polyethylene and allows the pressure-sensitive adhesive tape 10 to be used in applications such as duct tape.

In another embodiment, the woven fabric has a polymer coating 300 on the side of the fabric 100 opposite the adhesive 200 as shown in FIG. 2. This coating is preferably a PVC (polyvinyl chloride) or an acrylic. Preferably the coating is matte and therefore diffuses light so as to be less noticeable on film when used as a gaffers tape. Preferably the polymer coating 300 is colored to match the color of the fabric 100. The polymer coating typically adds 100% weight to the fabric and must be thorough in coverage with no pin holes. The full face coverage of the PET/acetate fabric enhances this characteristic in the tape.

Other additives may be present in the warp yarns, weft yarns, and/or adhesive to provide other properties to the tape 10. These other additives include, but are not limited to colorants, flame retardants, antimicrobial agents, wetting agents, surfactants, and odor control agents.

EXAMPLE

For a first example, a 60×48 fabric was formed using 40 d SDY (spin draw yarn) polyester warp, sized, and 150 d acetate weft. The fabric was coated with a synthetic rubber adhesive and exhibited excellent properties for tear in both directions without any type pretreatment of the fabric. Tape tensile was 20.1 lbs/inch with elongation of 20%. Tear strength in the warp was 0.487 $lb_f$. For a second example, a 72×54 40 d woven fabric was formed with SDY polyester warp sized and 150 d acetate weft fabric for evaluation that had warp tensile of 28 lbs/inch and elongation of 30%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A hand tearable tape comprising a woven fabric having a first side and a second side, an adhesive on the first side of the fabric and a polymer coating on the second side of the fabric, wherein the woven fabric comprises polyester warp yarns and acetate weft yarns, wherein the polyester warp yarns are less than about 45 denier, wherein the fabric has a tensile strength of between 18 and 60 lbs/inch, and wherein the fabric and polymer coating are colored.

2. The hand tearable tape of claim 1, wherein the tape is a medical tape.

3. The hand tearable tape of claim 1, wherein the acetate weft yarns are between about 100 and 200 denier.

4. The hand tearable tape of claim 1, wherein the woven fabric has a plain weave construction.

5. The hand tearable tape of claim 1, wherein the woven fabric comprises between about 50 and 130 warp ends per inch and about 30 and 65 weft ends per inch.

6. The hand tearable tape of claim 1, wherein the adhesive is a pressure sensitive adhesive.

7. The hand tearable tape of claim 1, wherein the polyester warp yarns are monofilament.

8. The hand tearable tape of claim 1, wherein the polyester warp yarns are multifilament.

9. The hand tearable tape of claim 1, wherein the polymer coating is polyvinyl chloride or an acrylic.

10. The hand tearable tape of claim 1, wherein the fabric has less than 15% open area.

11. A hand tearable tape comprising a woven fabric having a first side and a second side, an adhesive on the first side of the fabric and a polymer coating on the second side of the fabric, wherein the woven fabric comprises polyester warp yarns and acetate weft yarns, wherein the fabric has a tensile strength of between 18 and 60 lbs/inch, wherein the fabric has less than 15% open area, and wherein the fabric and polymer coating are colored.

12. The hand tearable tape of claim 11, wherein the fabric has less than 10% open area.

13. The hand tearable tape of claim 12, wherein the polyester warp yarns are less than about 45 denier.

14. The hand tearable tape of claim 11, wherein the fabric has less than 5% open area.

* * * * *